United States Patent
Fukunaga et al.

(10) Patent No.: US 6,290,908 B1
(45) Date of Patent: *Sep. 18, 2001

(54) WATER QUALITY METER AND WATER MONITORING SYSTEM

(75) Inventors: Masao Fukunaga; Tamio Ishihara, both of Hitachinaka; Koji Saito, Mito; Katsutoshi Yamada, Hitachinaka; Hideo Enoki, Niihara-gun; Sadao Mori, Tsuchiura; Ryo Miyake, Tsukuba; Takao Terayama, Ushiku; Masatoshi Kanamaru, Inashiki-gun, all of (JP)

(73) Assignee: Hitachi, Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/281,098

(22) Filed: Mar. 29, 1999

(30) Foreign Application Priority Data

Mar. 30, 1998 (JP) .................................................. 10-083208
Jul. 15, 1998 (JP) .................................................. 10-200071

(51) Int. Cl.[7] .................................................. G01N 15/00
(52) U.S. Cl. .................. 422/68.1; 73/64.55; 73/863; 73/863.31; 422/82.05; 210/85
(58) Field of Search .................. 210/85, 94, 96.1, 210/459, 188, 257.1; 216/2; 422/68.1, 70, 82.05; 436/39, 124, 177, 180; 73/53.01, 64.55, 64.56, 863, 863.01, 863.02, 863.23, 863.31, 863.24, 863.25, 866.5; 435/291; 96/155

(56) References Cited

U.S. PATENT DOCUMENTS

| | | | |
|---|---|---|---|
| 5,160,604 | * 11/1992 | Nakamura et al. | 73/863.24 |
| 5,304,487 | * 4/1994 | Wilding | 435/291 |
| 5,646,863 | * 7/1997 | Morton | 210/85 |
| 5,821,405 | * 10/1998 | Dickey et al. | 73/53.01 |
| 5,824,270 | * 10/1998 | Rao | 422/82.05 |
| 5,869,004 | * 2/1999 | Parce et al. | 73/863 |

FOREIGN PATENT DOCUMENTS

| | | | |
|---|---|---|---|
| 54-124789 | * 9/1979 | (JP) | 73/863.31 |
| 583100 | * 12/1977 | (SU) | 210/96.1 |

OTHER PUBLICATIONS

Journal of The Society of Instrument and Control Engineers, vol. 33, No. 8, issued Aug. 1994.

* cited by examiner

Primary Examiner—Joseph W. Drodge
(74) Attorney, Agent, or Firm—Kenyon & Kenyon

(57) ABSTRACT

A water quality meter is composed of a plurality of analyzing units for analyzing water samples introduced from a water distribution pipe, each analyzing unit including a reagent mixing cell and a measuring cell, and a liquid introducing unit integrated with the analyzing units, which is composed of a single member in which a plurality of fluid flow paths for feeding various types of liquid including the water sample into the analyzing unit are formed. Furthermore, the cells and the plurality of three-dimensional fluid flow paths formed in the single member are fabricated by a micro-fabrication technique using photo-curing resin.

24 Claims, 7 Drawing Sheets

WATER QUALITY METER AND WATER MONITORING SYSTEM

BACKGROUND OF THE INVENTION

The present invention relates to a water quality meter to measure the quality of drinking water distributed via pipes and a water quality monitoring system using the water quality meter.

As an example of a water quality monitoring system, an automatic water quality measurement system known to be used in Tokyo, and its design specification is described in a paper of The Journal of The Society of Instrument and Control Engineers (Japan), Vol. 33, No. 8, August 1994, pp. 649–653.

In this water quality measurement system, a water quality meter is provided at each of the piping subsystems composing a water supply piping network at a water supplier, and it continuously measures the water quality of each piping system. Furthermore, the measured water quality is transmitted to a control center with a telemeter at regular intervals.

As a means for measuring the water quality for end users, a manual analysis in which the distributed water of the end user is sampled and manually analyzed with a reagent or an off-line measurement using a portable water quality meter is performed.

In a conventional water quality monitoring system such as the above-mentioned system, since a water quality meter is provided in each water piping subsystem, the number of the provided meters is comparatively small, and the average quality of water distributed in each subsystem can be determined. However, the conventional system has a problem in that the quality of water which end users drink is not determined.

The quality of water is measured and controlled at a water supplying facility. However, the water quality is degraded while water passes through a water distribution piping network. For example, the concentration of chlorine to maintain the bactericidal activity in drinking water is decreased due to chemical reactions with the materials composing the water distribution system or with components contained in the drinking water. Also, the chromaticity of drinking water is increased by coloring due to stains on the inside surfaces of the pipes, and the turbidity of drinking water is also increased due to the peeling of deposits on the inside surfaces of the pipes. Although the above-mentioned degradation of water quality is naturally caused in main pipes, this degradation is more strongly caused in end side pipes in a water distribution piping network or in pipes in the houses of end users. It is well known that the concentration decrease of residual chlorine in water is proportional to the staying time in water. The staying time of chlorine in water is longer in the end side pipes than in the main pipes in which water always flows. Therefore, the concentration of residual chlorine is decreased in the end side pipes. Furthermore, in the extreme case, the concentration of chlorine becomes zero, and water without the bactericidal activity may be drunk. The concentration decrease of residual chlorine causes the degradation of the bactericidal activity of water, which may cause the breeding of microbes, and especially of pathogenic microbes (for example, O-157 coliform bacilli), and further cause a social problem concerning the safety and health of people. On the other hand, increasing the concentration of chlorine in drinking water to a higher level to maintain the bactericidal activity of drinking water causes the problem of a bleaching powder smell or a safety problem of producing harmful substances such as a chloric residuum of trihalomethane.

As to the chromaticity and the turbidity of drinking water in the end side pipes also, problems similar to the above-mentioned problems are caused due to the long staying time of water. In particular, a water storage tank is used in aggregate residences or business establishments, and if the water storage tank is not well managed, the above problems are often caused.

In an ideal water quality management system, the quality of water in the end side pipes, which end users drink, is monitored, and is adequately managed based on the results of the monitoring. The size of a conventional water quality meter, for example, 1.2 m×1.8 m×0.6 m, is so large that it cannot be provided in places such as a typical house or aggregate residences. Since the price of a conventional water quality meter or the cost of providing a conventional water quality meter is high, the number of conventional water quality meter provided in typical houses or aggregate residences is small. Furthermore, since professional expertise is required for the maintenance of a conventional water quality meter and the consideration for the safety of a meter is important, it is difficult to use a conventional water quality meter in typical houses. Thus, conventional water quality meters have not been provided at a desirable pipe location in the neighborhoods of houses of end users or of aggregate residences.

On the other hand, although the quality of water at the end side of a water distribution piping network can be measured by a manual analysis or with a portable water quality meter, it takes a long time for measuring results to be obtained, and water quality data cannot be continuously obtained, which makes it impossible to determine the range of variation in water quality in a day, or the transient behavior of water quality.

In water quality data, the maximum and minimum values in a transient state are important, and the development of a system and a control method of the system to reduce the variation in these values is mandatory. Therefore, a manual analysis or a portable water quality meter is not suitable for the above continuous monitoring system.

In a very rare example, by restricting measurement categories and places in which water quality detectors are provided, for example, by providing residual chlorine concentration detectors at the rate of one per ten to thirty-plus thousand end users at end side pipes of a water distribution system, an on-line water quality measurement has been performed. However, conventional water quality meters used in the above water quality measurement can measure only one category, and are also large and expensive meters similar to ones used in water purifying facilities. Therefore, places in which such meters are set cannot be easily obtained, and it is also to difficult to obtain sufficiently detailed measurements of water quality.

SUMMARY OF THE INVENTION

The present invention has been achieved in consideration of the above described problems, and is aimed at providing a water quality meter and a water quality monitoring system in which water quality meters can be set at places near the end side pipes of a drinking water distribution system, and further can measures a plurality of measurement categories.

To attain the above object, the present invention provides a water quality meter attached at a location on a pipe in a water distribution system which supplies water that is obtained by purifying raw water as drinking water to each end user via a water distribution piping network, the water quality meter comprises:

at least one analyzing unit for analyzing a water sample introduced from the location on the pipe; and a liquid introducing unit composed of a single member in which a plurality of fluid flow paths for feeding various types of liquid including the water sample into the analyzing unit are formed.

Moreover, in the above water quality meter, the member composing the liquid introducing unit is made of plastic which is cured by ultraviolet irradiation.

Further, in the above water quality meter, the analyzing unit includes a measurement flow path in which liquid flows, and a plurality of apertures open to the measurement flow path, with liquid to be fed into the analyzing unit from the liquid introducing unit being introduced to the measurement flow path through the apertures.

Furthermore, the above water quality meter further includes a plurality of containers for liquid to be fed into the analyzing unit, the liquid in the containers being fed into the analyzing unit via the fluid flow paths in the liquid introducing unit.

Still further, in the above water quality meter, liquid stored in each of the containers is one of a reagent prepared corresponding to a measurement category, washing water to wash the measurement flow path, and reference water to be used for correcting a result of a measurement performed by the analyzing unit.

Also, in the above water quality meter, the containers are detachably attached to the water quality meter.

Additionally, in the above water quality meter, the analyzing unit is fabricated by using a micro-fabrication technique.

On top of that, in the above water quality meter, a plurality of analyzing units is connected to the liquid introducing unit.

Moreover, in the above water quality meter, a plurality of analyzing units analyzes the same measurement category.

Also, the present invention provides a water quality monitoring system for monitoring the quality of water distributed by a water distribution system including water purifying facilities to purify raw water taken in from rivers, lakes, and/or wells to a quality suitable for drinking water, water distribution facilities for distributing the water purified by the water purifying facilities, a water quality control center for monitoring and controlling the water purifying facilities and the water distribution facilities, and a water distribution piping network for feeding the purified water to end users, the water quality monitoring system comprises:

water quality monitoring meters set at predetermined locations in the water distribution piping network, each of the water quality monitoring meters including at least one analyzing unit for analyzing a water sample introduced from the location on the pipe; a liquid introducing unit composed of a single member in which a plurality of fluid flow paths for feeding various types of liquid including the water sample into the analyzing unit are formed; and a transmission unit for transmitting to the control center;

wherein results of measurements performed by each of the water quality meters are transmitted to the water quality control center via the transmission unit of the water quality meter.

Further, in the above water quality monitoring system, each of the water quality meters is set in one of a manhole, a fire hydrant, a water meter box, a utility in the house of an end user, all of which are provided in the water distribution network.

Still further, in the above water quality monitoring system, the transmission between the control center and each of the water quality meters is performed with a radio transmission.

Furthermore, in the above water quality monitoring system, each of the water quality meter includes a solar battery and a storage battery connected to the solar battery via a diode, and the water quality meter is powered by energy fed from the solar battery and/or the storage battery.

DETAILED DESCRIPTION OF THE EMBODIMENTS

Figure 2:
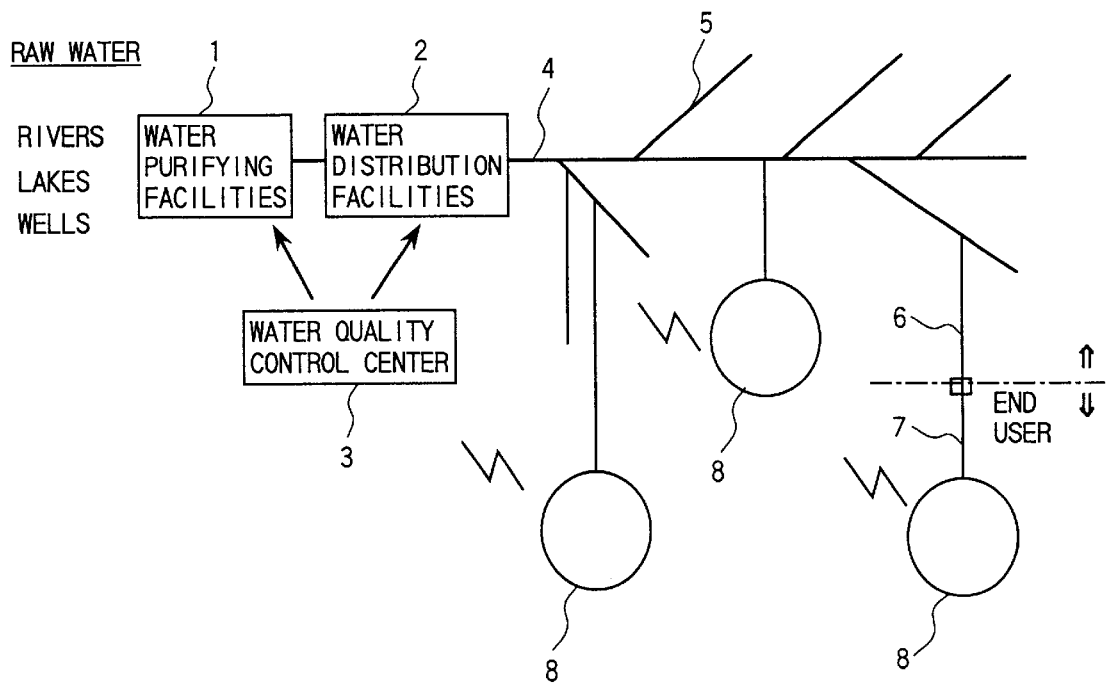
FIG. 2 shows an example of the composition of a drinking water distribution system using a water quality monitoring system with water quality meters of the embodiment according to the present invention.

Hereafter, details of the embodiments will be explained with reference to the drawings. FIG. 2 shows an example of a basic composition of a drinking water distribution system using a water quality monitoring system with water quality meters of the embodiment according to the present invention. Raw water taken from rivers, lakes, wells, and so on is purified to make the water quality suitable for drinking water by the water purifying facilities 1, and is sent to the water distribution facilities 2. The drinking water output from the water distribution facilities 2 is introduced into a water quality meter 8 via a water distribution system main pipe 4 and a water distribution subsystem main pipe 5, or further via a water supplier sub-pipe 6 and an end-user side pipe 7. Each water quality meter includes a transmission means, and can perform the transmission with a water quality control center 3. Information on the quality of the distributed drinking water which has been measured in an on-line manner by the water quality meters 8 is transmitted to the water quality control center 3 by a radio means, a line transmission method, a transmission satellite, etc. The water quality control center 3 then processes the received information, and controls the water purifying facilities 1 and the water distribution facilities 2 so as to ensure that the quality of distributed water is in a state suitable for drinking water.

Figure 3:
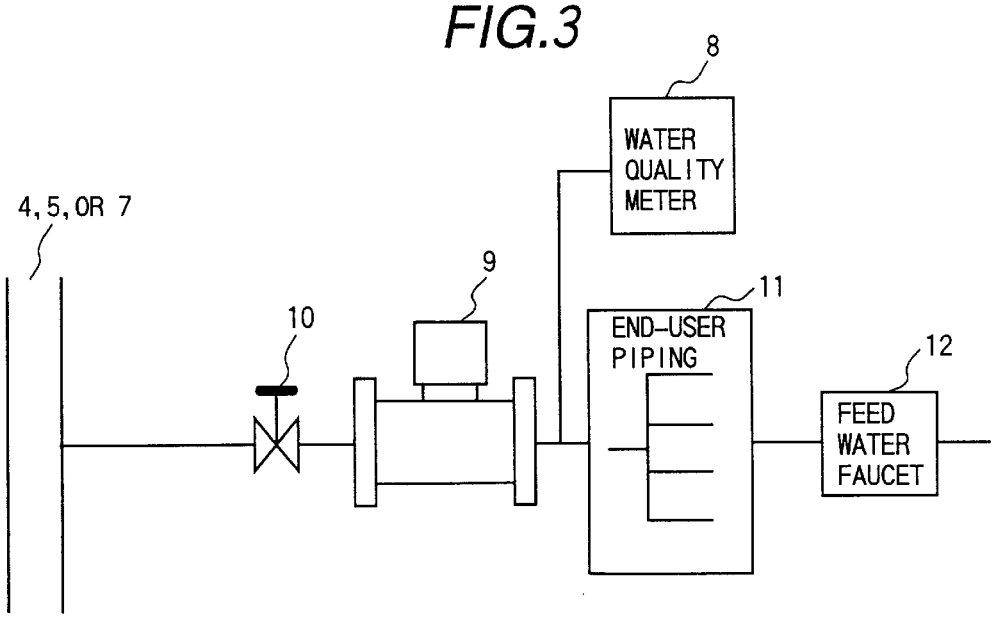
FIG. 3 shows an example of a method of setting a water quality meter at an end user side in a water quality monitoring system of an embodiment according to the present invention.

FIG. 3 shows an example of a method of setting a water quality meter at an end user side in a water quality monitoring system of an embodiment according to the present invention. The distributed drinking water branched from the water distribution subsystem main pipe 5 on the water supplier side, the water supplier side sub-pipe 6, or the end-user side pipe 7, enters the end-user piping 11 via a shut off valve 10 and a water meter 9, and a plurality of measurement categories for the quality of the drinking water is simultaneously measured by the water quality meter 8. The end-user piping is a network system composed of pipes, and some of the drinking water is fed to an end user from a location on the end user piping 11 via a feed water faucet 12 such as a water tap faucet. The water quality meter 8 can be attached before or after the water meter 9, or in a water meter container box, and further has a size such that it can be easily set in a manhole, a fire hydrant, a utility in the house of an end user, or in the vicinity of a water tap faucet. Although the composition of the water quality meter 8 is later explained in detail, in accordance with the embodiment of the present invention, the water quality meter 8 can be easily set in a space of 10 cm×20 cm×20 cm.

Figure 4:
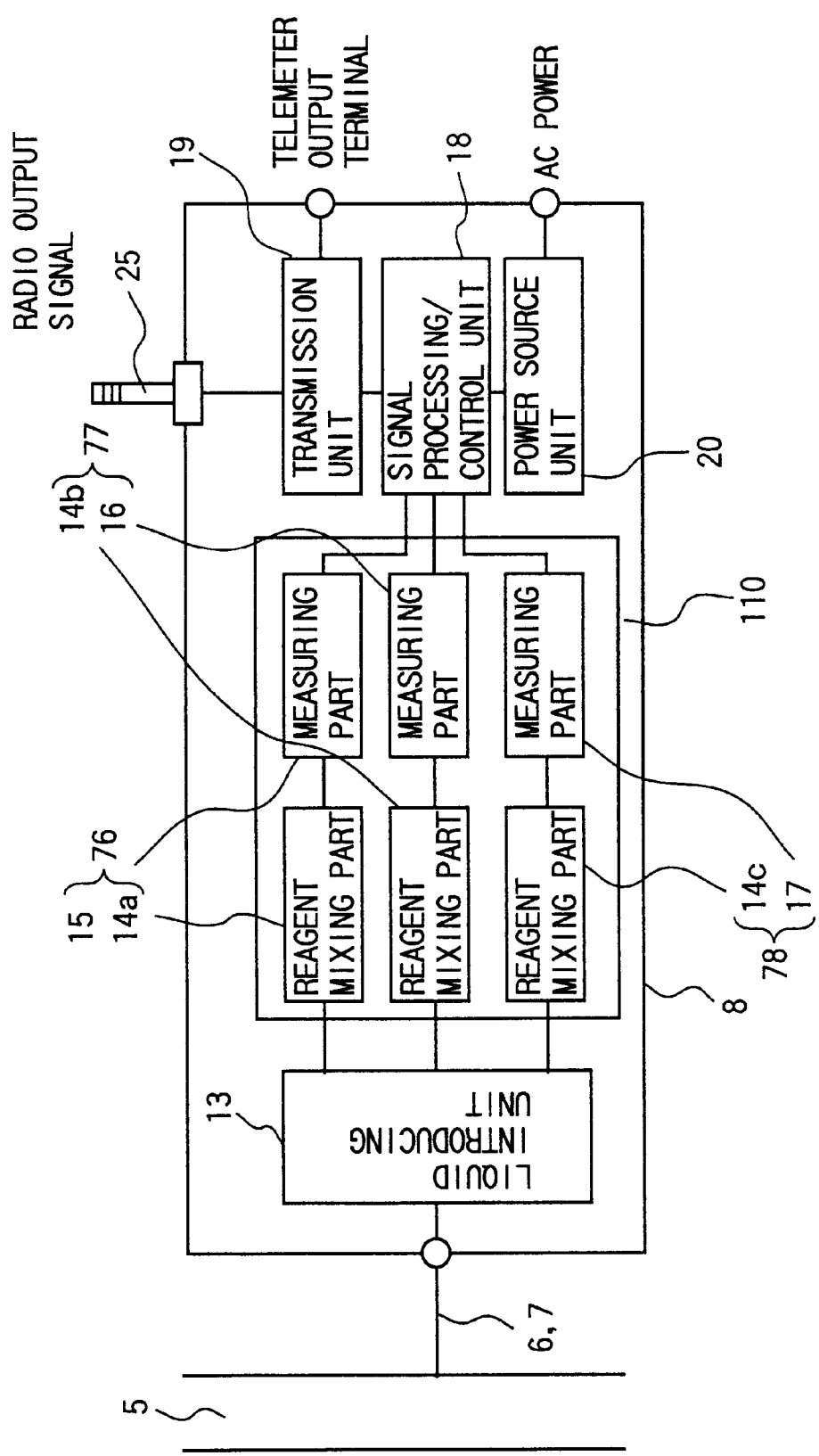
FIG. 4 is a schematic block diagram showing the internal composition of a water quality meter of the embodiment according to the present invention.

FIG. 4 is a schematic block diagram showing the internal composition of a water quality meter of the embodiment. Water sample introduced from the pipes 4, 5, 6, and 7 via a liquid introducing unit 13 is measured for each measurement category by the mixing and analyzing unit 110, using a predetermined measuring sequence, and the measured value for the category is converted to an electrical signal. Further, the electrical signal is sent to a signal processing/control unit 18. The mixing and analyzing unit 110 is composed of a plurality of reagent mixing parts 14a–14c provided for the respective measurement categories, and a plurality of measuring parts 15–17 corresponding to the respective reagent mixing parts 14a–14c. Each of the plurality of reagent mixing parts 14a–14c and the plurality of measuring parts 15–17 is formed as a cell with a module structure. Therefore, it is easy to provide cells corresponding to the number of required measurement categories. The measurement categories are the concentration of residual chlorine, the turbidity, the chromaticity, the conductivity, pH, the concentration of chloric residua such as trihalomethane, the number density of pathogenic microbes, and so forth. The signal processing/control unit 18 receives power from a power source unit 20, and processes result data of measurements performed by the mixing and analyzing unit 110. The result data processed by the signal processing/control unit 18 are converted to signals for transmission by a transmission unit 19. Further, the converted signals for transmission are transmitted to the water quality control center 3 by a radio means, or a telemeter via an exclusive transmission line or a public transmission line.

By applying a micro-fabrication technique, the mixing and analyzing unit 110 can be fabricated in a very small size, and the power consumption and the amount of the water sample and mixed reagent can be reduced. Accordingly, a battery can be used as the power source unit 20, and withdrawal collection or evaporation of the exhaust water becomes possible, which makes constructing work for equipment to process the exhaust water from the water quality meter 8 unnecessary. In addition, wiring works for data transmission from the water quality meter 8 also become unnecessary because a radio data transmission line is used. Thus, the freedom of choice in locating the water quality meter 8 is greatly expanded.

Figure 1:
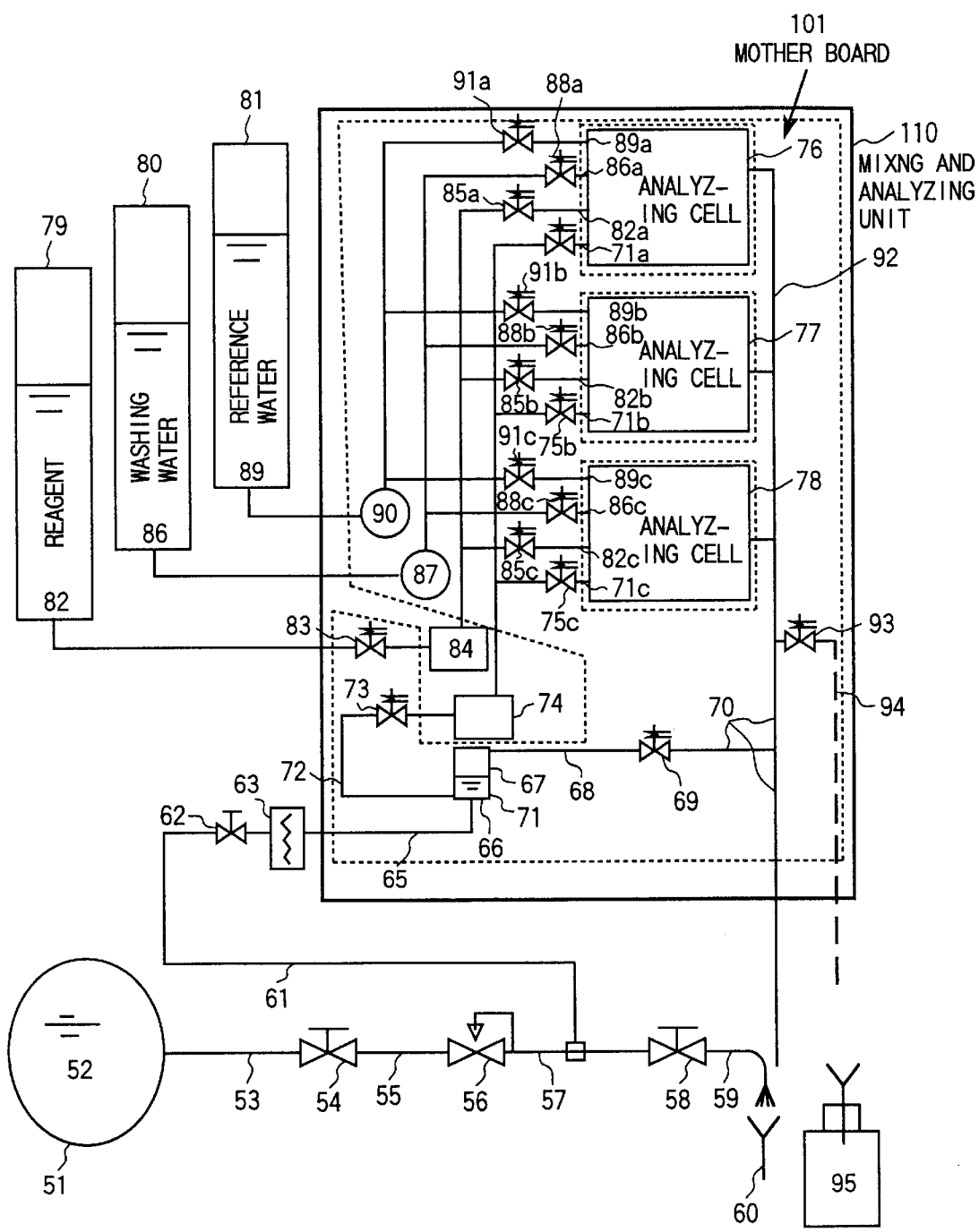
FIG. 1 is a block diagram showing the composition of a water quality meter of an embodiment according to the present invention.

In the following, the detailed composition of a water quality meter of the embodiment will be explained with reference to FIG. 1. The water quality meter 8 is constructed by attaching pumps (74, 84, 87, and 90), electromagnetic valves (69, 73, 83, 93, 75a–75c, 85a–85c, and 91a–91c), and analyzing cells (76, 77, and 78), to a mother board 101. Here, diaphragm valves and metering pumps (syringe pumps) are used for the pumps 87 and 89 and the pumps 74 and 84, respectively. Moreover, fluid flow paths are formed in the regions surrounded by dotted lines shown in FIG. 1, inside the mother board 101. Drinking water 52 flowing in a pipe 51 at the water supplier or end user side is sampled via a pipe 53. Further, the sampled drinking water passes through a manual valve 54, a pipe 55, a depressurization valve 56, a pipe 57, a manual valve 58, and is sent to an exhaustion conduit 60 from a pipe 59.

A part of the water sample 52 whose pressure is maintained at a constant value is branched from the pipe 57 by the pipe 61, and is introduced to a filter 63 for removing comparatively large extraneous substances in the branched water via a manual valve 62. Further, the water is introduced to a degassing tank 66 via a flow path 65 in the mother board 101. Inside the degassing tank 66, bubbles contained in the water sample 52 gather in the upper part of the degassing tank 66, and this gas is exhausted at appropriate intervals to the exhaust water conduit 60 from the mother board 101 via an electrode 69 and a flow path 70.

Water sample 71 in the tank 66, from which bubbles are removed, is introduced to the metering pump 74 via a flow path 73 and the electromagnetic valve 73. Moreover, the water sample 71 is selectively sent to the plurality of analyzing cells 76, 77, and 78, each analyzing cell analyzing an independent measurement category, via the plurality of electromagnetic valves 75a, 75b, and 75c, and a plurality of fluid inlet holes 71a, 71b, and 71c. The shape and size of the analyzing cells 76–78 are the same, and the arrangement of the flow paths in the cells is also the same, so that the cells interchangeable with each other. Also, these analyzing cells are detachably held on the upper face of the mother board 101. Furthermore, a plurality of cartridges 79, 80, and 81 containing liquid are held detachably held on the outside of the mother board 101, and liquid contained in each cartridge is fed to the mother board 101. Liquid 82 (reagent) from the cartridge 79 is selectively sent to the analyzing cells 76–78, the electromagnetic valve 83 and the metering pump 84, via one of the plurality of electromagnetic valves 85a–85c that corresponds to the selected analyzing cell, and also via one of the plurality of flow inlet holes 82a–82c that corresponds to the selected analyzing cell. Similarly, liquid 86 (washing water) from the cartridge 80 is selectively sent to the analyzing cells 76–78 by the metering pump 87, via one of the plurality of electromagnetic valves 88a–88c that corresponds to the selected analyzing cell, and also via one of the plurality of flow inlet holes 86a–86c that corresponds to the selected analyzing cell. Also, liquid 89 (reference water) from the cartridge 81 is selectively sent to the analyzing cells 76–78 by the metering pump 90, via one of the plurality of electromagnetic valves 91a–91c that corresponds to the selected analyzing cell, and also via one of the plurality of flow inlet holes 89a–89c that corresponds to the selected analyzing cell.

Each analyzing cell (whose structure is later explained in detail) is composed of a reagent mixing part in which mixing or a reaction of the water sample with the liquid fed from each cartridge is performed; or liquid fed from each cartridge flows through along with a measuring part for measuring liquid sent from the reagent mixing part for a predetermined measurement category, and is shaped by a microfabrication technique. Thus, although the size of this analyzing cell is very small, its function is equivalent to that which one set of analyzing equipment of a conventional size possesses. Last, exhaust water 92 whose analysis has been finished is expelled to the outside of the water quality meter 8 via flow paths 70. If the exhaust water 92 is harmful, or there is not a water exhaust utility, the exhaust water 92 is expelled into an exhaust water storage container 95.

Figure 5:
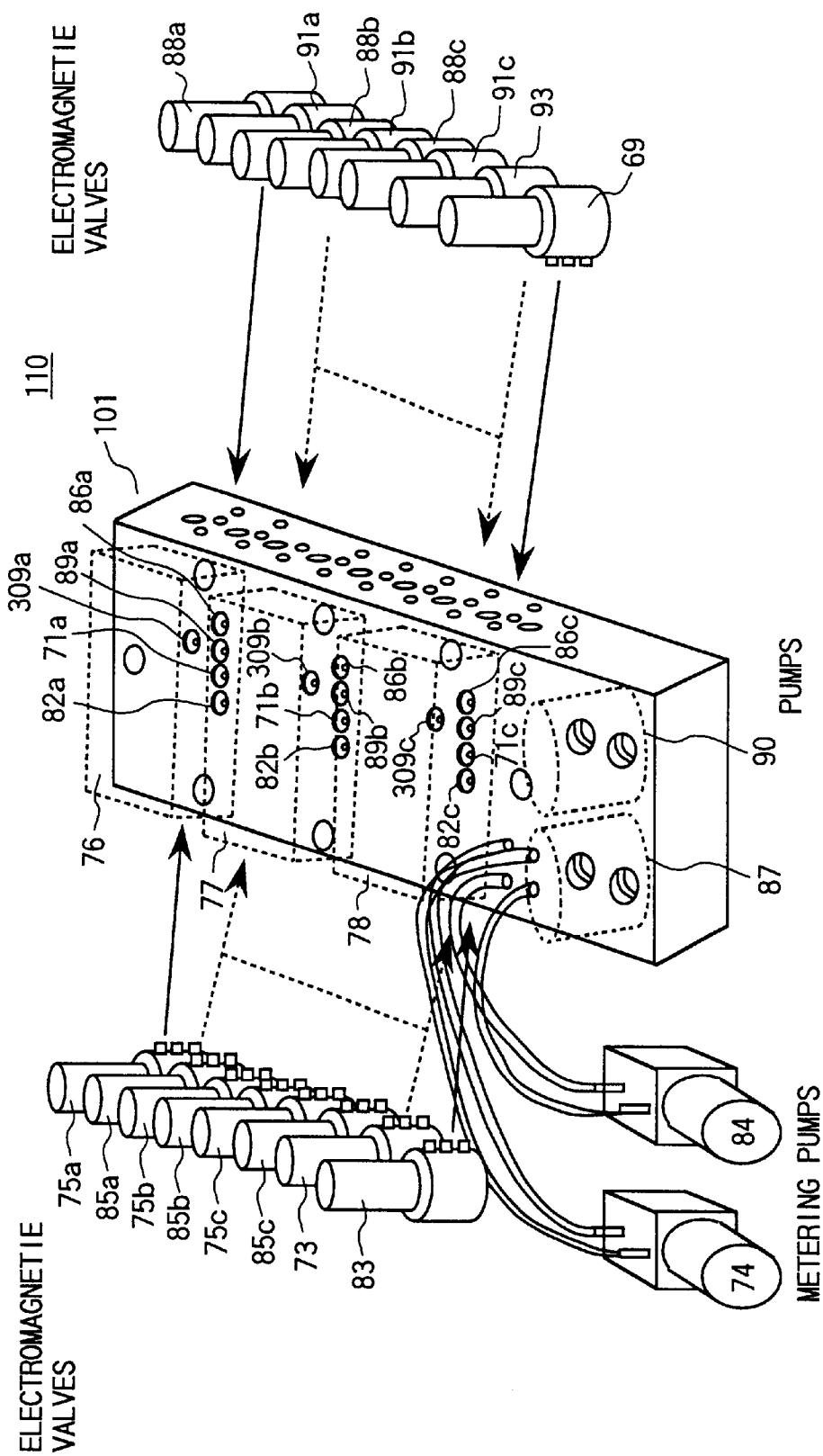
FIG. 5 shows the detailed structure of a mother board used in the embodiment according to the present invention.

Furthermore, in the following, details of the mixing and analyzing unit 110 will be explained with reference to FIG. 5. The shape of the mother board 110 is a rectangular parallelepiped, and there are connection holes for inputting and outputting water sample on the right side face of the mother board 110 with the electromagnetic valves 93 and 69 being attached to the corresponding holes. Moreover, the flow inlet holes 89a–89c and 82a–82c for inputting the reference water 89 and the reagent 82 are arranged longitudinally, and the electromagnetic valves 88a–88c and 91a–91c are attached to the corresponding holes. On both sides of each of the longitudinally arranged inlet holes, there is a pair of internal threads, and each of the electromagnetic valves 93, 69, 88a–88c, and 91a–91c, is fixed to the mother board 101 with screws by using the internal threads.

Similarly, there are flow inlet holes for inputting water sample on the left side face of the mother board 101, and the electromagnetic valves 83 and 73 are attached to the corresponding holes. Moreover, the flow inlet holes 71a–71c for inputting water sample and 86a–86c for inputting the washing water 86 are arranged longitudinally, and the electromagnetic valves 75a–75c and 85a–85c are attached to the corresponding holes. Also, on both sides of each of the longitudinally arranged inlet holes, there is a pair of internal threads, and each of the electromagnetic valves 83, 73, 85a–85c, and 75a–75c, is fixed to the mother board 101 with screws by using the internal threads.

On the other hand, on the upper face of the mother board 101, there are open holes are formed to communicate with the pumps 74, 84, and 87, so that pressure is applied to fluid flowing in the mother board 101 so as to send the fluid onward. Furthermore, the analyzing cells 76–78 are fixed to the upper face. These analyzing cells 76–78 are connected to the mother board 101 via the flow inlet holes 82a–82c, 71a–71c, 89a–89c, 86a–86c, and 309a–309c.

The main fluid flow paths formed in the mother board 101 are explained below with reference to FIG. 6. All the internal fluid flow paths ( paths 65, 68, 70, 72, 92, 94, etc.) are three-dimensionally formed in the motherboard 101. On the back face of the mother board 101, there are flow inlet holes for introducing the water sample 52, the reagent 82, the washing water 86, and the reference water 89. As mentioned above, the shape of the mother board 101 is a rectangular parallelepiped, and on its outer surface, there are a plurality of flow inlet or connection holes and a plurality of internal threads for holding valves, pumps, analyzing cells, etc. via sealing elements without connection pipes on the surface of the mother board 101.

Figure 6:
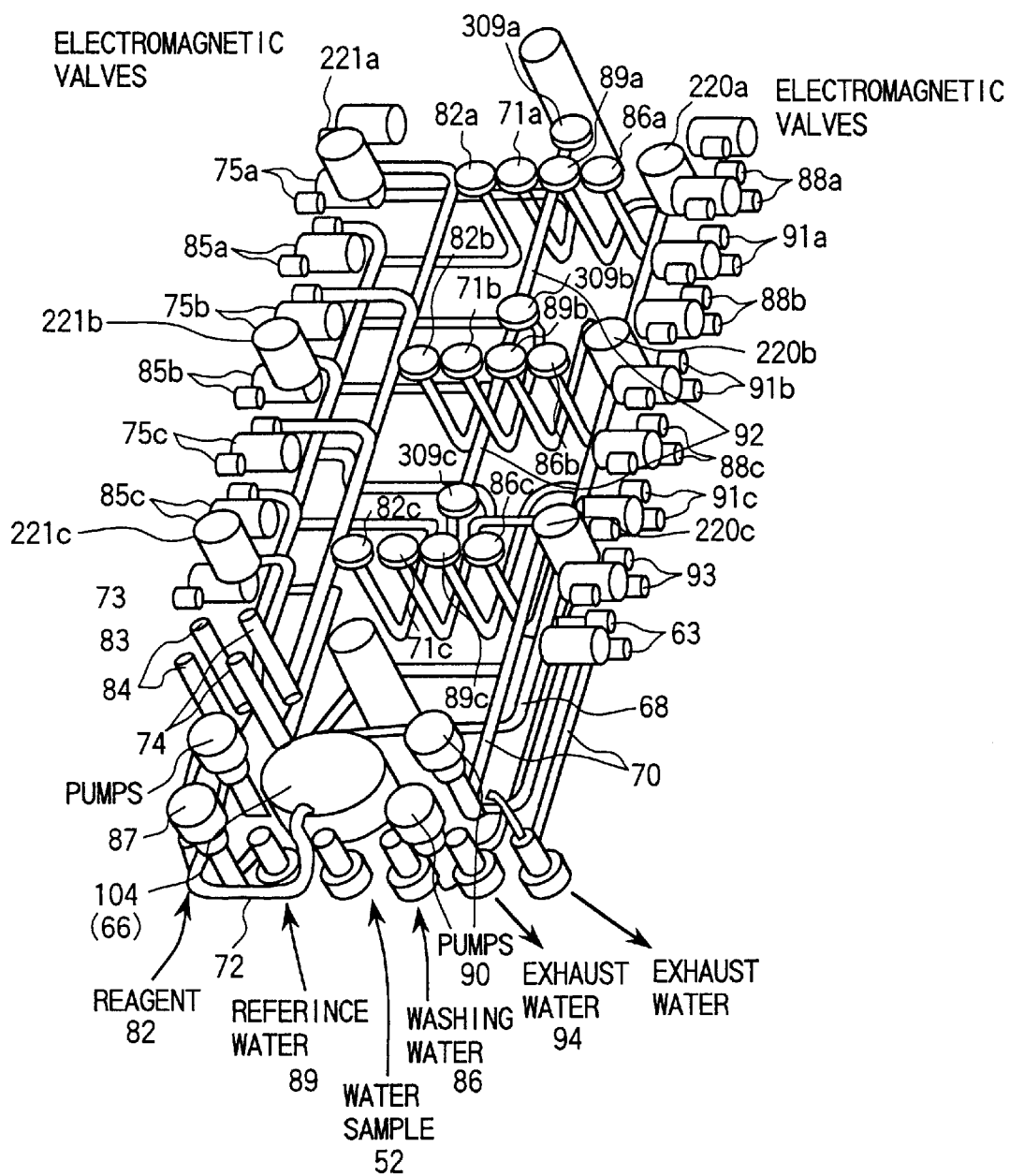
FIG. 6 is a perspective view showing a three-dimensional structure of fluid flow paths used in the mother board.

If the resin parts are removed from an illustration of the mother board 101, and only the internal fluid flow paths are illustrated, the paths are seen as shown in FIG. 6. Such three-dimensional fluid flow paths have rarely been realized. If one intends to form such stereoscopic fluid flow paths, the paths should be conventionally formed by superimposing a plurality of plates in which two-dimensional paths are mechanically formed. This embodiment adopts a photoforming method in which a three-dimensional shape is formed by irradiating a part of the shape in liquid ultraviolet-curing type plastic in a transparent container with an ultraviolet laser beam. To form the three-dimensional fluid flow paths in this embodiment, parts of the three-dimensional fluid flow paths in ultraviolet-curing-type plastic are not irradiated with an ultraviolet laser beam, and these parts remain as liquid plastic. Afterward, by washing out the liquid plastic which has not cured, the remaining solidified plastic parts complementary to the three-dimensional fluid flow paths can be obtained. In this embodiment, transparent ultraviolet-curing-type epoxy resin is used so that states inside the fluid flow paths can be observed. The photoforming method can cheaply and quickly form a three-dimensional shape using only three-dimensional data of the shape (which are used for CAD), without a shaping mold which and further improves the reliability of the connection parts of the fluid flow paths and the external equipment such as valves, pumps, and so on.

As shown in FIG. 6, the sizes or shapes of the fluid flow paths in the mother board 101 can be freely designed while satisfying a constraint in that two points are connected with the shortest three-dimensionally smooth-curve route without steep bending, which causes very little stagnation of dust and bubbles in fluid in the fluid flow paths.

Furthermore, since a branch or a connection in the flow paths can be formed at an optional position inside of the mother board 101 without a coupling element, mixing or separating of fluid can be performed at an optional position inside of the mother board 101. The degassing tank 66 can also be formed in a space with the three-dimensional shape of a degassing tank 104 shown in FIG. 6.

In the above monitoring system according to the present invention, the plurality of pumps and electromagnetic valves are controlled by a sequence control method, and drinking water 52 sampled from the drinking water distribution pipe 51 and liquid in each of the plurality of cartridges are introduced into the corresponding reagent mixing part. Further, In the reagent mixing part, the introduced liquid reacts with the water sample, and the result of the reaction is measured by the measuring part. Here, In cases where a reagent is not used, no reagent is introduced.

In a typical case according to the embodiment, the water sample is drinking water distributed by a water distribution system and a reagent such as DPD or orthotolidine reacting with chlorine and causing color development. Moreover, washing water such as dilute chloric acid, neutral detergent, etc.; and reference water such as pure water, calibration water, etc. are selected as liquid 86 in the cartridge 80 and liquid 89 in the cartridge 81, respectively. The water sample, the reagent, the washing water, and the reference water are introduced to the corresponding analyzing cells at a predetermined interval using a sequence control method. In the above case, the analyzing cells 76, 77, and 78 are used as a residual chlorine concentration meter, a chromaticity meter, and a turbidity meter, respectively. The reagent liquid 82 is introduced only to the analyzing cell 76 allocated as the residual chlorine concentration meter. Naturally, a measurement category can be changed by changing the type of reagent, and the allocation of each analyzing cell to some one of the required measurement categories is optional.

In the residual chlorine concentration meter, the degree of color development due to the reaction of the water sample and the reagent is measured by an absorptiometric method.

In the chromaticity meter, a reagent is not used, and the absorbance of water sample is measured. However, since the absorbance of the water sample is low, a comparison measurement method is adopted using the reference water (pure water), and a base level of the zero absorbance is calibrated for a predetermined period. As for the turbidity meter, neither reagent nor reference water is used, but impurity particles are counted. Further, the total number is converted to the turbidity value.

Moreover, if an analyzing cell with electrodes is used, the conductivity or pH of the water sample can be measured without changing the structure of the analyzing cell.

A predetermined quantity of the washing water liquid 86 is introduced to each analyzing cell at prescribed time intervals, and washes the fluid flow paths in the analyzing cell, the electrodes, and so on. Substances washed out from the analyzing cells are expelled from the mixing and analyzing unit 110 along with the water sample 71 or the reference water 89.

Here, although one cartridge is used for the reagent in this embodiment, a plurality of cartridges can be provided for reagents, and various types of reagent can be used for the different measurement categories for which a reagent is necessary, by using a selection valve, for example.

In the following, details of the structure of each of the analyzing cells 76, 77, and 78 shown in FIG. 4 will be explained with reference to FIG. 7 and FIG. 8. Although only the analyzing cell 76 is explained below, the structure of the other cells 77 and 78 are the same as that of the cell 76, and explanations for the structures of the cells 77 and 78 have therefore been omitted.

Although the principle of measurement performed in each analyzing cell is different from those of the other analyzing cell (the absorptiometry for a predetermined wavelength is carried out in the residual chlorine concentration meter and the chromaticity meter, and a fine particle number coefficient method is adopted for the turbidity meter. Moreover, the conductivity or pH can be measured by using an analyzing cell with electrodes.), the analyzing cells have a module composition in which both the size and shape, and the arrangement of the internal fluid flow paths, are common among the analyzing cells. Although the three analyzing cells are detachably attached to the upper surface of the mother board 101 in this embodiment, the number of analyzing cells is not restricted to three. That is, by changing the arrangement of the internal fluid flow paths in the analyzing cells, the number of analyzing cells mounted on the mother board 101 can be freely changed. Also, the arrangement of the analyzing cells is arbitrary. By selecting a liquid or a reagent for an analyzing cell according to a measurement category, and setting a measurement sequence, it is possible to set the analyzing cell to perform a required measurement function.

In another example, all of the analyzing cells can be set so as to measure the same measurement category. By setting a plurality of analyzing cells measuring the same measurement category on the mother board 101, the reliability of the measurement for that category can be improved. Accordingly, even if a malfunction occurs in one of the analyzing cells, the measurement can be continued by using the remaining normal cells, which can extend the life time of the total monitoring system.

Figure 7:
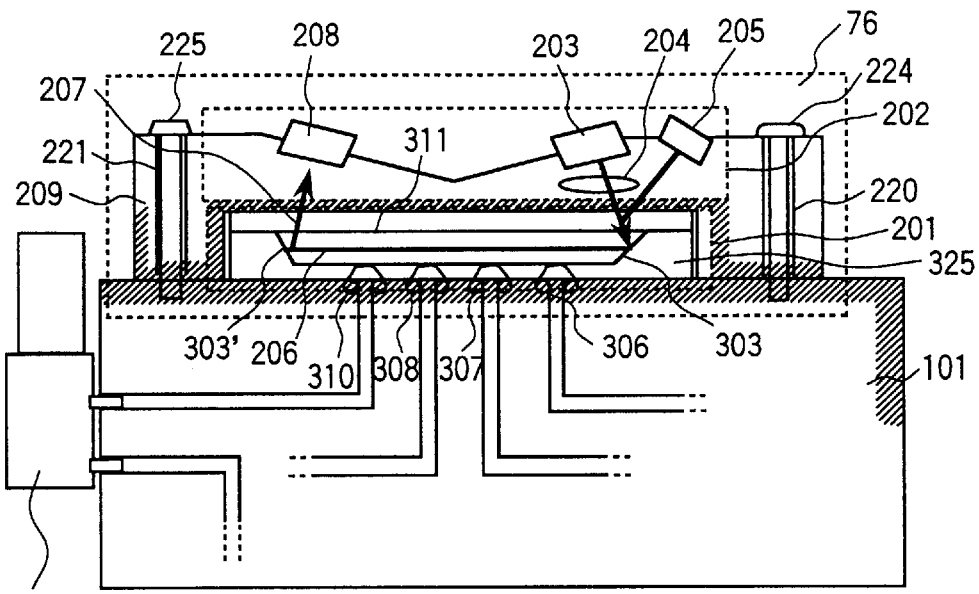
FIG. 7 is a vertical cross section showing the composition of a mixing and analyzing unit in a water quality meter of the embodiment according to the present invention.
Figure 8:
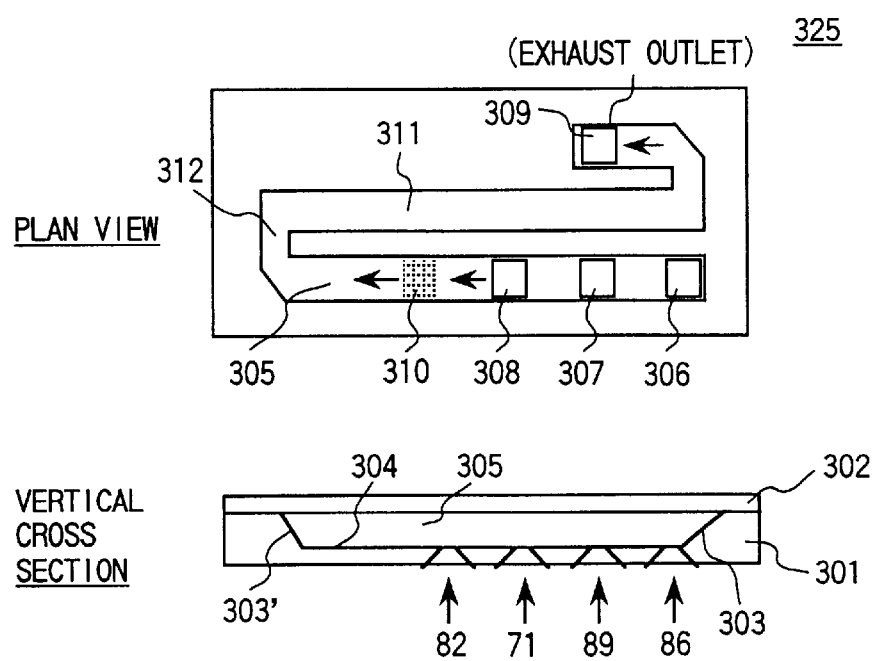
FIG. 8 shows the composition of an analyzing cell in each mixing and analyzing unit.

As shown in FIG. 7, each analyzing cell is composed of the reagent mixing part 201 (flow cell substrate 325) and the measuring part 202 ( measurement cell substrate 209). The structure of the reagent mixing part (flow cell substrate 325) is explained in detail below with reference to FIG. 8. The flow cell substrate 325 has a duplex layered structure of a silicon substrate 301 and a Pyrex glass cover 302, and is fabricated by the micro-fabrication technique. An S-shaped fluid flow path 305, an inclined face 303 and a flat bottom face 304 are formed in the substrate 301 by shaping a wafer of highly pure silicone using an anisotropic etching. Furthermore, a plurality of rectangular penetrating holes 306, 307, 308, and 309, and a mesh-type hole 310 in which fine holes with a diameter of several micrometers are formed in a mesh state with a pitch of 100–200 $\mu$m, are also on the back side of the substrate 301. All of the holes 306–310 are connected to the fluid flow path 305. Moreover, the cover 302 is connected to the upper surface of the substrate 301 by an anodic bonding method. The substrate 301 and the cover 302 are connected to each other to which a predetermined voltage is applied at a high temperature in a vacuum state in a wafer size. Afterward, the wafer is cut to as a required size for use. The usage size, which depends on the shape of the flow path 305, is about 1 cm×2 cm.

One of the various types of liquid (water sample 71, reagent 82, washing water 86, and reference water 89) is selected and fed to each agent mixing part 201 (flow cell substrate 325), by selectively driving the electromagnetic valves and the pumps attached to the side faces of the mother board 101. In this embodiment, the reference water 89, the washing water 86, water sample 71, and the reagent 82 are fed to the holes 306, 307, 308, and 310, respectively. The liquid flows in the flow path 305, is introduced to the straight path 311, and finally expelled to the outside of the analyzing cell.

Here, in this embodiment, the liquids from the cartridges are injected to the penetrating holes so that at the further upstream the position in the fluid flow path, the cleaner (purer) the water that flows. By the above liquid injection method, the whole of the flow path 305 can be cleaned. In addition, by filling the flow path 305 with the cleanest water, for example, the reference (pure) water, when measurements are not being made, and introducing the other liquid only for measurements, the degradation of measurement sensitivity due to the contamination of the flow paths 305 can be prevented.

Furthermore, all of the various types of liquid flow in different paths each in the mother board 101. That is, the various types of liquid are separately fed to the flow cell substrate 325, and never mixed until the liquid enters the flow path 305 in which a measurement such as the absorbance measurement is executed. Therefore, since the mixing of the various types of liquid occurs just before the measurement, the contamination of the flow paths in the mother board 101 due to the mixing of the various types of liquid is kept as low as possible, which can result in highly accurate measurements.

Next, the measuring part 202 (measurement cell substrate 209) will be explained. A light emitting element 203 such as an LED, a laser diode, etc., a lens system for converging a light beam emitted from the light emitting element 203 at the inclined face 303 in the straight path 311, and a light detecting element 205 for monitoring changes in the quantity of the light beam are arranged in the measurement part 202. The converged light beam 206 which has been transmitted through the straight path 311 is reflected by the inclined face 303' opposite to the inclined face 303, and returns to the measurement part 202. The light beam which has returned to the measurement part 202 is measured by a light detecting element 208 provided in the measurement part 202. The light emitting element 203, the light detecting elements 205 and 208, the lens system 204, and the straight path 311 are attached to the measurement cell substrate 209 so that their relative positions are fixed. Further, the measurement cell substrate 209 is detachably attached to the mother board 101.

Although explanations for the other analyzing cells for the chromaticity and the turbidity are omitted, for these cells, the shape and size of the analyzing cells 76–78 are common, as is the arrangement of flow paths.

The residual chlorine concentration meter for which the analyzing cell 76 is used is explained below. In this residual chlorine concentration meter, while the washing water 86 and the reference water 89 are not fed, the water sample 71 and the reagent 82 are fed to the concentration meter at a predetermined ratio, and mixed in the flow path 305. Here, the reagent 82 is injected into the water sample through the mesh-type hole 310. By passing the reagent 82 through the mesh-type hole 310, the reagent 82 can be homogeneously injected into the water sample, which will enable the reagent 82 to diffuse in the water sample for a short time. Accordingly, the color development reaction of the water sample 71 and the reagent 82 is quickly completed with the degree of color development being proportional to the residual chlorine concentration. The mixture of the water sample 71 and the reagent 82 in which the color development reaction has been completed is introduced to the straight path 311, and the degree of color development is measured by the absorptiometric method. While measuring the absorbance of the mixture, the flow of the mixture is temporarily stopped so as to stabilize the measured value. After the measurement, the measured mixture 312 is expelled through the penetrating hole 309. When calibrating the sensitivity for or the zero point of the degree of color development proportional to the residual chlorine concentration, the reference water 89 whose chlorine concentration was measured in advance is fed into the analyzing cell 76, and the degree of color development is measured using the above-explained procedures. This measured value for the degree of color development is used as the reference value to correct the measured values for the degree of development. The washing water 86 is fed into each analyzing cell to wash and remove mineral or plant contaminants in its reagent mixing part (especially in the straight path 311) corresponding to the grade of contamination.

Here, in the structure of the analyzing cell according to the present invention, if fine extraneous substances or bubbles adhere to the inside of the flow path 311, the quantity of the light beam 206 transmitting through the path 311 changes considerably, which makes it impossible to correctly measure the absorbance of the mixed liquid. Since the fine extraneous substances or bubbles are very small, and adhere to many different locations, all of the extraneous substances or bubbles cannot removed by the usual procedure of washing the flow paths in each analyzing cell. In the present invention, a plurality of washing liquid feeding patterns other than the usual washing liquid feeding procedure is prepared, and any one of the patterns can be selected.

The prepared washing liquid feeding patterns are as follows.

(1) The water sample 71 is fed as the washing liquid. That is, since the pump 74 for feeding the water sample 71 is a metering pump, this pump can feed the washing liquid using high pressure although the flow rate of the washing liquid has a definite value. The fine extraneous substances and bubbles are removed by the water sample 71, which is fed at a higher pressure than a water sample fed for a usual measurement.

(2) The washing water 87 and/or the reference water 81 is fed as the washing liquid. That is, since the pumps for feeding the washing water 87 and the reference water 81 are diaphragm pumps, and feed liquid with a pulsating flow, the fine extraneous substances and bubbles are removed by the pulsating flow.

(3) The washing water 86 (which is more effective if it includes surfactant) is fed to the straight path 311, and remains there for a time. Afterward, the path 311 is washed by the water sample 71. This pattern is effective for contaminant which cannot be removed by a change in the flow rate, as in pattern (2).

In accordance with the present invention, the fine extraneous substances and bubbles can be removed by using one or a combination of the above washing liquid feeding patterns, which can provide a more reliable water quality meter. Moreover, the washing liquid feeding pattern can be designated from the water quality control center 3 by a remote transmission.

Figure 9:
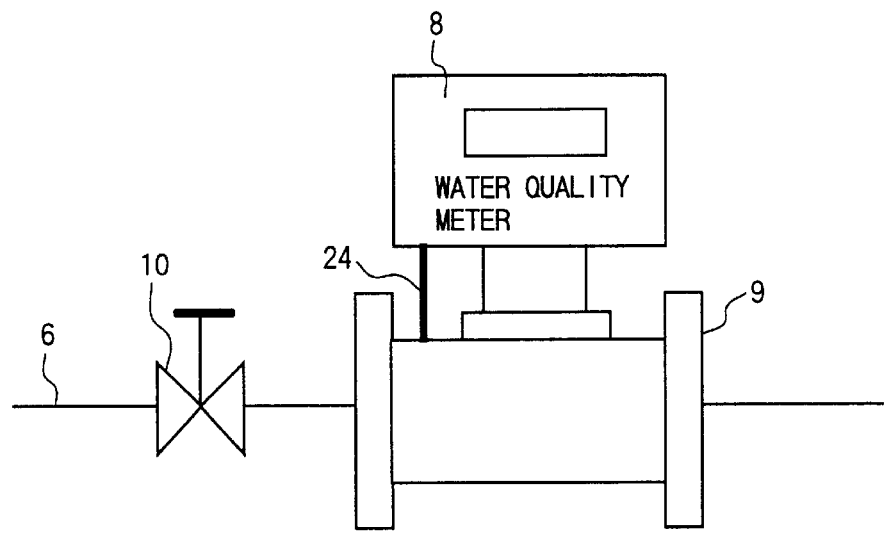
FIG. 9 shows another example of a method of setting a water quality meter at an end user side in the water quality monitoring system of the embodiment according to the present invention.

In FIG. 9, another water quality monitoring system of a composition different from that of the system shown in FIG. 3 is shown. In the embodiment shown in FIG. 9, the water meter 9 and the water quality meter are integrated. Since the water quality meter according to the present invention can, by adopting the micro-fabrication technique, be made smaller while retaining the ability of to measure a plurality of measurement categories, the water quality meter can be incorporated into the water meter 9. The water distributed to each end user flows through the water meter 9 via the water supplier side sub-pipe 6 and the shut off valve 10, and the flow rate of the water is measured by the meter 9. Simultaneously, part of the water is fed into the water quality meter 8 via a water sample-introducing pipe 24. According to this composition, the integrated water meter and water quality meter are contained in the box for the water meter 9, and can be attached to a water distribution pipe for the end user. Thus, a special space and/or an special attachment labor for the water quality meter become unnecessary, and the integrated water meter and water quality meter can be as easily attached as a conventional water meter.

Figure 10:
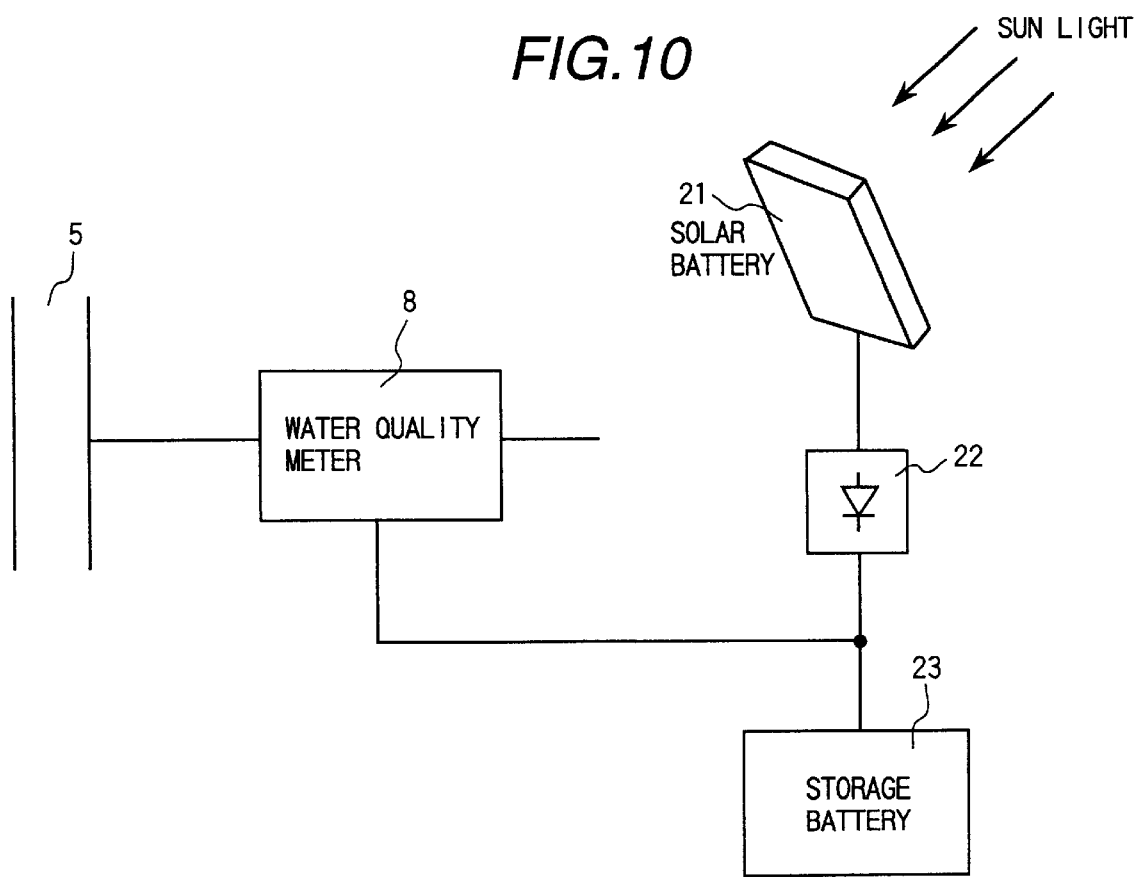
FIG. 10 shows an example of a water quality monitoring system of another embodiment according to the present invention.

In FIG. 10, another water quality monitoring system of a composition different from that of the system shown in FIG. 9 is shown. In the embodiment shown in FIG. 10, power fed to the water quality meter is generated in the system itself with solar batteries. The power generated by the solar batteries is fed to the water quality meter via a diode 22, and surplus power is stored in a storage battery 23. If the sunlight energy is not obtained at night or on a rainy day, the storage battery 23 backs up power supplied to the water quality meter by discharging the stored energy. The diode 22 is provided as a protection means for preventing a reverse current flow to the solar batteries 21 when discharging energy from the storage battery 23. According to the above composition, by selecting the proper capacity for the solar batteries 21 and that for the storage, battery 23, an autonomous operation of the water quality meter without external power becomes possible. Equipment or labor to secure AC power is not necessary, which can remove the limitation for selecting the location of the water quality meter and reduce the cost of fabrication.

Since the above-explained water quality meter 8 is located at the house of each end user, the control center 3 can control the quality of water distributed to each end user. In another example, the water quality meters are located at houses at a ratio of one to thirty-plus houses, which can reduce the quantity of transmitted data between the control center 3 and the water quality meters to one thirtieth or less of the original volume, and greatly reduce the load of data processing in the control center 3. Furthermore, it becomes possible to control the quality of water distributed to end users with the remarkably higher accuracy than a conventional system which can control the quality of water at the end user side only at a ratio of one to several hundreds of thousands of houses.

Furthermore, since the size of the water quality meter 8 according to the present invention has been considerably decreased with the micro-fabrication technique, the quantity of the water sample or reagent used for the water quality measurements can be reduced to a level of micro-litters. Accordingly, the time interval for refills of the reagent, washing water, etc. can be extended by more one month even with continuous measurements.

The above embodiments are summarized as follows.

(1) The water quality meter according to the present invention is set at the end side part of the water distribution piping network, near or in the house of each end user, and a control center performs collective water quality control based on information transmitted from each water quality meter.

(2) The water quality meter is set in a manhole, a fire hydrant, a water meter box, a utility (for example, under a drain in the house of an end user), etc. Thus, the possibility that ordinary people might touch the water quality meter is decreased, and so the safety can be assured.

(3) The sample inlet unit, the reagent mixing part, and the measuring part, which generally increase the size of a measurement apparatus, are made much smaller by adopting the micro-fabrication technique. The size of the water quality meter can be decreased to one-thousandth of that of a conventional water quality meter by using the presently developed micro-fabrication technique.

(4) The three-dimensional fluid flow paths in the analyzing cell are formed by using ultraviolet-curing-type plastic, which can make possible a tubeless structure. Thus, the mixing and analyzing unit can be made smaller, and the reliability of the unit can also be improved.

(5) The fabrication and an installation cost of the water quality meter are decreased by making the meter smaller, and since the micro-fabrication technique is used in the silicon semiconductor element processing, the fabrication cost can be greatly decreased even further by mass-producing water quality meters according to the present invention.

(6) The quantity of liquid used for the water quality measurement can be reduced to a level of micro-litters because the size of the water quality meter is very small. Thus, the period for refills of the reagent can be extended by more one month even if the measurements are continuously performed. Moreover, the quantity of exhaust water is very small, and if an exhaust water withdrawal and collection, or evaporation method is adopted, the installation of exhaust water equipment is not necessary.

(7) The reagent, the reference water, and so on, which are consumed in the measurements, are each stored in cartridges and fed to the analyzing cells each, which can make refilling them very easy.

(8) The decrease in size of the water quality meter also greatly decreases its power consumption. Thus, a built-in battery or a solar battery can be used as a power source, and transmission wiring also becomes unnecessary by using a radio circuit as a signal transmission means.

(9) The composition of the fluid flow paths is such that the various types of liquid to be used are not mixed before reaching each analyzing cell, which can prevent contamination in the flow paths. Furthermore, a plurality of penetration holes for introducing various types of liquid each are formed in a flow path in each analyzing cell, and these various types of liquid are introduced from the respective penetration holes so that the further upstream the position in the fluid flow path, the cleaner the liquid (the purer the water) that flows, which can suppress contamination in the flow path in the analyzing cell.

(10) Since it is assumed that fine extraneous substances or bubbles will adhere to the inside surface of the flow path in the analyzing cell if a comparatively large variation occurs in the results of the measurement, one of a variety of prepared washing liquid feeding patterns other than the usual washing water feeding procedure is selected and executed to remove the fine extraneous substances or bubbles.

In accordance with the present invention, the effects described below can be expected.

(1) Since a water quality meter with a size of one-thousandth of that of a conventional water quality meter can be provided, the flexibility in the installation of the meter can improved.

(2) Since a water quality meter of a small size and minimal power consumption can be achieved, it is possible to construct an on-line water quality monitoring system which can measure a plurality of measurement categories without wiring by using a battery as a power source and a radio transmission means.

(3) By adopting a module structure for the analyzing cells, the selection, combining, or changing of the measurement categories is easy, which enables it to be more flexible in responding to changes in the measurement sequence.

(4) By applying a photo-forming method using ultraviolet-curing in the formation of three-dimensional fluid flow paths with three-dimensional CAD data of the flow paths, the three-dimensional fluid flow paths can be formed without using a mold, by which the water quality meter can be cheaply and quickly fabricated.

(5) Since a micro-sized sampling and analyzing unit can be fabricated, the quantity of liquid needed for the water quality measurement is reduced, which can considerably extend the time interval for refills of the liquid.

(6) Since various types of liquid to be used for the measurement are not mixed until just before the measurement is performed, the contamination of the internal fluid flow paths can be prevented, which can greatly improve the accuracy of the water quality measurement.

As explained above, in accordance with the present invention, it is possible to provide a micro-sized water quality meter with a high reliability, and a water quality monitoring system using the water quality meter.

Speaking in greater detail, since a water quality meter has a size of one-thousandth of that of a conventional water quality meter can be provided, it is possible to provide a water quality meter of a very small size and a low water sample flow rate. Accordingly, the water quality meter can be driven by an internal battery, and continuous measurements over a long period are possible with a only small quantity of reagent. Therefore, special wiring and piping are not necessary to install the water quality meter, which can greatly reduce the installation cost. Thus, the water quality monitoring system can be very easily constructed.

Furthermore, since the analyzing cells have a common module structure, it is possible to realize a water quality meter for a variety of measurement categories, in which there is a great deal of freedom in the selection and combination of the measurement categories.

What is claimed is:

1. A water quality meter sized and configured for attachment to a location on a pipe so as to draw water out of said pipe prior to its supply to an end use in a water distribution system which supplies water that is obtained by purifying raw water as drinking water to each of a plurality of end users via a water distribution piping network, said water quality meter comprising:

a plurality of analyzing units each of, which includes a measurement flow path in which liquid flows for introducing a water sample into said measurement flow path from said location on said pipe, and analyzing said water sample; and a liquid introducing unit comprising a single member in which a plurality of fluid flow paths for feeding a plurality of types of liquid including said water sample into said plurality of analyzing units is formed.

2. A water quality meter according to claim 1, wherein ultraviolet curable plastic is used for said member comprised in said liquid introducing unit; and said plurality of fluid flow paths inside said member being shaped by ultraviolet irradiation.

3. A water quality meter according to claim 2, wherein a degassing tank for removing bubbles from said water sample is provided at an intermediate position in said fluid flow path into which said water sample is introduced.

4. A water quality meter according to claim 1, wherein each of said analyzing units includes a plurality of apertures open to the measurement flow path in that analyzing unit, with liquid to be fed into that analyzing unit from said liquid introducing unit being introduced to said measurement flow path through said apertures.

5. A water quality meter according to claim 4, further including a plurality of containers for liquid to be fed into each of said analyzing units, said liquid in said containers being fed into each of said analyzing units via said plurality of fluid flow paths in said liquid introducing unit.

6. A water quality meter according to claim 5, wherein liquid stored in each of said containers is one of a reagent prepared corresponding to a measurement category, washing water to wash the measurement flow paths in each of said analyzing units, and reference water to be used for correcting a result of a measurement performed by each of said analyzing units.

7. A water quality meter according to claim 5, wherein the cleanest liquid of said types of liquid stored in said containers is introduced from an aperture located at the furthest upstream position in the measurement flow paths in each of said analyzing units.

8. A water quality meter according to claim 7, wherein the measurement flow paths in each of said analyzing units are filled with liquid introduced from said aperture located at said furthest upstream position while in a non-measurement state.

9. A water quality meter according to claim 6, wherein an aperture for introducing a reagent is a mesh-type aperture.

10. A water quality meter according to claim 5, wherein various types of liquid including said water sample are fed to each of said analyzing units in a sequence determined corresponding to a required measurement category.

11. A water quality meter according to claim 10, wherein a water sample with a pressure higher than that which is usual for a measurement operation is fed into the measurement flow paths in each of said analyzing units in a washing operation for removing extraneous substances and/or bubbles inside said measurement flow path in each of said analyzing units.

12. A water quality meter according to claim 10, wherein washing water or reference water is fed into the measurement flow paths in each of said analyzing units with a pulsating flow in a washing operation for removing extraneous substances and/or bubbles inside said measurement flow path in each of said analyzing units.

13. A water quality meter according to claim 10, wherein after washing water is fed into the measurement flow paths in each of said analyzing units and has remained there, a water sample is fed into said measurement flow path, in a washing operation for removing extraneous substances and/or bubbles inside said measurement flow path in each of said analyzing units.

14. A water quality meter according to claim 5, wherein said containers are detachably attached to said water quality meter.

15. A water quality meter according to claim 4, wherein said plurality of fluid flow paths in said liquid introducing unit are formed separately from each other, and corresponding to each type of liquid to be fed to each of said analyzing units.

16. A water quality meter according to claim 4, wherein each of said analyzing units is fabricated by using a microfabrication technique.

17. A water quality meter according to claim 4, wherein each of said analyzing units includes a member constructed by connecting a silicon wafer processed using anisotropic etching and a Pyrex glass cover with an anodic bonding method, the measurement flow paths in each of said analyzing units being formed between said silicon wafer and said Pyrex glass cover.

18. A water quality meter according to claim 4, wherein a film made of water-repellent resin is formed on the inside surface of the measurement flow path in each of said analyzing units.

19. A water quality meter according to claim 4, wherein said analyzing unit includes a light source and a light detection device, the measurement flow paths in each of said analyzing units are radiated with a light beam emitted from said light source, and said light beam which has passed through the measurement flow paths in each of said analyzing units is detected by said light detection device.

20. A water quality meter according to claim 1, wherein each of said analyzing units is formed with a module structure, and is detachably attached to said liquid introducing unit.

21. A water quality meter according to claim 1, wherein each of said analyzing units respectively analyze different measurement categories.

22. A water quality meter according to claim 21, wherein said different measurement categories are selected from the group consisting of concentration of chlorine, the turbidity, the chromaticity, the pH, the concentration of chloric residue, and the number of pathogenic microbes, and combinations thereof.

23. A water quality meter according to claim 1, wherein said plurality of analyzing units analyze the same measurement category.

24. A water quality meter according to claim 1, being set in a location of the group consisting of a manhole, a fire hydrant, a water meter box, and a utility in the house of an end user.

* * * * *